United States Patent [19]
Schaefer et al.

[11] Patent Number: 5,565,364
[45] Date of Patent: Oct. 15, 1996

[54] METHOD FOR THE ANALYSIS OF A COMPONENT OF A MEDICAL SAMPLE

[75] Inventors: Rainer Schaefer, München, Germany; Bela Molnar, Budapest, Hungary; Christoph Berding, München, Germany; Peter Wolf, Habach, Germany; Fridl Lang, Tutzing, Germany

[73] Assignee: Boehringer Mannheim GmbH, Mannheim, Germany

[21] Appl. No.: 393,946

[22] Filed: Feb. 22, 1995

Related U.S. Application Data

[63] Continuation of Ser. No. 95,910, Jul. 22, 1993, abandoned.

[30] Foreign Application Priority Data

Jul. 25, 1992 [DE] Germany ............................ 42 24 621.0

[51] Int. Cl.$^6$ ............................ G01N 30/86; G01N 30/88
[52] U.S. Cl. ............................ 436/43; 436/161; 436/164; 395/22; 395/23; 395/25; 395/76
[58] Field of Search ............................ 395/22, 23, 25, 395/26, 76; 436/43, 56, 161, 164, 171, 172, 174

[56] References Cited

U.S. PATENT DOCUMENTS

| | | | |
|---|---|---|---|
| 4,157,871 | 6/1979 | Anderson et al. | 356/341 |
| 4,204,837 | 5/1980 | Sternberg et al. | 23/236 |
| 4,965,725 | 10/1990 | Rutenberg | 364/413.1 |
| 5,011,608 | 4/1991 | Damjanovic | 210/656 |
| 5,120,421 | 6/1992 | Glass et al. | 204/406 |
| 5,177,994 | 1/1993 | Moriizumi et al. | 422/83 |
| 5,218,529 | 6/1993 | Meyer et al. | 364/413.01 |

OTHER PUBLICATIONS

Zupan, et al., "Neural Networks: A New Method For Solving Chemical Problems Or Just A Passing Phase?", *Analytica Chimica Acta* 248: 1–30 (1991).

Gemperline, et al., "Nonlinear Multivariate Calibration Using Principal Components Regression And Artificial Neural Networks", *Anal. Chem.* 63: 2313–2323 (1991).

Ham, et al., "Improved Detection Of Biological Substances Using A Hybrid Neural And Infrared Absorption Spectroscopy", *IEEE* 1: I–227–I–232 (1991).

Ungar, et al., "Adaptive Networks For Fault Diagnosis And Process Control", *Computers Chem. Engng.* 14: 561–572 (1990).

Sundgren, et al., "Artificial Neural Networks And Gas Sensor Arrays: Quantification Of Individual Components In A Gas Mixture", *Meas. Sci. Technol.* 2: 464–469 (1991).

Long, et al., "Spectroscopic Calibration And Quantitation Using Artificial Neural Networks", *Anal. Chem.* 62: 1791–1797 (1990).

*Primary Examiner*—Lyle A. Alexander
*Attorney, Agent, or Firm*—Hoffmann & Baron

[57] ABSTRACT

A method for the analysis of a component of a medical sample with the aid of an autoanalyzer, in which the sample is reacted with a reagent system and a physically measurable quantity X resulting from the reaction of the sample with the reagent system is measured in order to determine at least one measured value R for a specified sample and in which this at least one measured value R is further processed with the aid of a processing unit in a processing stage in order to determine an analytical result A. In the processing stage of the invention, use is made of the results of a neural net training, in which, for a number of standard samples for which the analytical result A is known, at least one measured value R, or a measurement result derived from several measured values $R_i$, is applied to the input of a neural net.

16 Claims, 5 Drawing Sheets

METHOD FOR THE ANALYSIS OF A COMPONENT OF A MEDICAL SAMPLE

This is a continuation of application Ser. No. 08/095,910 filed on Jul. 22, 1993, now abandoned.

BACKGROUND OF THE INVENTION

The invention relates to a method for the analysis of a component of a medical sample by means of an autoanalyzer, in which a reaction of the sample with a reagent system is carried out and a physically measurable quantity X resulting from the reaction of the sample with a reagent system is measured. At least one measured value R is determined here for a specified sample. This is converted into an analytical result A in a processing unit of the analyzer.

Many different methods can be used in medical laboratory analysis for determination of the desired analysis result A, where fully automatic analyzers are mostly used for carrying out the method. The samples are, as a rule, body fluids, especially blood and urine, and are investigated in order to obtain an analytical result A concerning one of the components contained in them.

The result A is usually (in quantitative analyses) the concentration C of the component. In qualitative analyses it is the assignment of the sample (with regard to the investigated analyte) to a medico-analytical state, for example, the statement that the analysis result is positive or negative. More than two states, for example, 'high', 'normal', and 'low', are sometimes also usual here. However, other medically significant results of an analysis of a medical sample are also to be regarded as an analytical result A as defined by the invention, for example, a statement on the presence of a disease made directly (that is, without any concentration value or any medico-analytical condition being indicated) from the analysis. This is at present still rather unusual, though the invention is creating new possibilities in this direction.

Expressed in terms of measurement electronics, the analytical result A is an analogous or logical state which is normally determined from at least one measured value R fully automatically and embodies an item of medically relevant information.

The analysis is always based on the reaction of the sample with one or more reagents (which are together known as the reagent system) suitable for the analysis of a specified component (usually known as the 'analyte' or 'parameter') of the sample. The reagents are mixed in the autoanalyzer with the sample, either all at once or at predetermined intervals. The details of the method of analysis, apart from specially discussed peculiarities in certain practical forms of the invention, are not of importance for the present invention.

Examples of common physically measurable quantities X include the determination of a color change by means of photometry; nephelometry and turbidimetry for measuring the turbidity of a sample; sensitive light detection by means of photomultipliers, when X is a fluorescence signal; or current- or voltage-measurement for the case where the quantity X is of an electrical nature in electrochemical tests. The physically measurable quantity X is generally measured with a suitable method and technically converted into an electrical measurement signal. The measured value of the measurement signal is the value R, which is a definite measure of the quantity X.

Autoanalyzers generally fully automatically determine an analytical result A, which is usually a concentration C, from at least one measured value R. Several measured values $R_i$ are frequently determined on one sample, where a derivative variable is calculated in the processing unit from at least two measured values and can be termed the measurement result. In simple cases, the measured value R, or the measurement result deduced from at least two measured values $R_i$, can be clearly and accurately linked with the concentration C by a simple functional relationship, usually known as the calibration curve. The measured value and the measurement result form here the calibration input variable of the calibration $Y=f(C)$.

In the evaluation it must always be taken into account that the analysis reactions are time-dependent. The situation is relatively simple when the reaction or series of reactions resulting in the measurable physical quantity X proceed very rapidly. In this case, the measured value R is determined at a point in time when the analysis reaction is essentially completed and is immediately used as the input calibration variable Y. This is known as an end-point determination.

Another relatively simple example is the case where a relatively slow reaction is decisive for the alteration of the quantity X with time and from which there results over a certain length of time a time-related alteration ('kinetic') of the measured value R which follows a linear or other simple functional relationship. X is repeatedly measured here at various measuring times $t_i$ within the above-mentioned period. A measurement result describing the kinetic (for example, the alteration $dR/dt(t_i)$ of the measured value R per time unit at a certain time) is calculated from the measured value $R_i(t_i)$ and serves as the input variable Y for the determination of the analytical result A.

The alteration of X with time often depends in a very complex manner on the kinetic behavior of a number of partial reactions, which play a role in the overall reaction of the analysis system with the sample. This results in a complex course of the time-related alteration of the quantity X, which is known as complex reaction kinetics. The invention is particularly directed at such cases of complex reaction kinetics.

Various known approaches exist for the evaluation of the complex reaction kinetics resulting from several overlapping chemical kinetics of the individual reactions. For example, an attempt can be made to describe the complex reaction kinetics in the form of separate differential equations for the partial reactions, where the function parameters of the differential equations correspond to measurable reaction kinetic values. The complexity of the actual reaction system, however, necessitates idealizing model hypotheses that restrict the validity range of the model results. For this reason, phenomenological models, in which the function parameters bear no direct relationship to the individual reactions, but are frequently interpreted as a measure of a specific determined property of the reaction under consideration, have been proposed. Finally, there exist purely statistical models for describing the reaction kinetics. Each of the approaches has certain advantages, though development of the model is very demanding in terms of cost, labor and time. The capacity of a model to adapt to altered conditions (for example, a change of the reagent composition or, in certain circumstances, just of the reagent batch) is nevertheless small, and the accuracy and reliability of the evaluation of the measurement results, and of the determination of the analytical results from this, leaves much to be desired.

The processing unit of the autoanalyzer, in addition to determining the concentration and/or a medico-analytical state from the measured values, usually fulfills a number of other functions that contribute to the determination of a correct analytical result A. These usually include the plausibility testing of the measured values, identification of the reagent production batch, recognition of other reagent and apparatus conditions, detection of errors, and, in some cases, the correlation of differing measurement data obtained on one and the same sample or of measurement data on several samples. The invention also relates to such supplementary functions of the processing unit.

OBJECTS AND SUMMARY OF THE INVENTION

An object of the invention is to make available a method of the type described at the outset with improved quality and reliability.

This object is achieved by using, in the processing stage, the results of a neural net training, in which at least one measured value or one measurement result, deduced from several measured values by predetermined methods, for a large number of samples for which the analytical result A is known, is applied to the input of a neural net. Preferably the analytical result A, or a known auxiliary value linked with the analytical result, is applied to the output of the neural net. However, this is not necessary in all cases. In the context of the invention, self-organizing neural nets (Self-Organizing Maps-SOM), in which the training takes place without any supervision ("non-supervised learning"), have also been successfully used.

A neural net is a data processing system largely organized in parallel. It consists of a network of processing elements, which are also known as neurons, connected to each other by what are known as neuronal interconnects. Each neuron has one or more inputs, and produces a signal at its output. The output signal is divided into several copies and applied as input signal to the inputs of those neurons that are connected with the output. The information stored in a neural net consists of the 'weights' of the interneuronal connections, including the base potentials of the neurons determined in the learning phase.

A neuron j can have, within the network, several weighted inputs, for example, from the neurons $1, \ldots, i$. The weights of the neuronal interconnects are indicated by $w_i$, and the outputs of the preconnected neurons by $x_i$. Positive and negative weights (potentiation and inhibition, respectively) are possible. The net input $ne_j$ is then $$net_j = \sum_i w_{ij} * x_i.$$

An external input $exinp_j$ can be added to the net input of a neuron. The neurons of a network then calculate in parallel (but asynchronously) a new activation state $a_j(t+1)$ from their old activation state $a_j(t)$ and an activation function $F_j$:

$$a_j(t+1) = F_j[net_j(t+1), exinp_j(t+1), a_j(t)].$$

The output state $o_j$ usually corresponds to the (internal) activation state $a_j(t+1)$. However, in some cases, a further transformation step takes place when an output function $f_j$ is used.

$$o_j(t+1) = f_j(a_j(t+1)).$$

Various neural nets differ in their topology, i.e., the arrangement of the neurons and of the neuronal interconnects in the net. The neurons usually form layers in which each neural net has at least one input layer and one output layer. The inputs of the neurons of the input layer together form the input of the neural net, whilst the outputs of the neurons of the output layer together form the output of the neural net. Further so-called hidden layers can be arranged between the input layer and the output layer. The structure (topology) of a neural net is determined by the number of layers, the number of neurons per layer, and the neuronal interconnects present.

One characteristic of the neural nets is that they can 'learn', by means of a neural net training. In practice, neural nets are used primarily for purposes of image-processing, where it is a matter of re-recognizing certain image patterns. During training of the neural net, image signals of certain patterns (for example, circles, squares, etc.) produced with a video camera are applied to the input, whilst a signal corresponding to the desired correct recognition is applied to the output of the neural net. If the neural net is suitably selected and configured for the task and the learning process is repeated sufficiently frequently, the neural net is able to classify unknown objects, that is, to assign them to one of the learned groups, even if the image does not correspond exactly to the learned pattern. The association and reconstruction of patterns are therefore basic accomplishments of known neural nets.

The function of a specified neural net is determined not only by its topology, but also by the algorithm used for processing the input signals into the output signals, and for the adaptation of the weights of the neuronal interconnects that takes place in the learning process. These are, in particular, the activation function, which determines the generation of the output of the individual neurons from the above-mentioned product sum, the output functions, and the algorithms used for the learning process, usually known as propagation functions.

The following are, among others, characteristics of neural nets:

1. They consist of very simple processing units (neurons) which each perform their own simple operation (signal reception, summation of the input signals, transformation of the summated inputs and passing on of signals). The task of each neuron is thus restricted to receiving input signals via the neuronal interconnects attached to its input and to producing an output signal via the above-mentioned calculation and making it available at its output. These steps are carried out in parallel by the neurons.

2. The specific information resides not only in the topology and in the base potentials of the neurons, but also in the weights of the interconnects. Various neural net types differ with regard to the rules by which the weights are fixed initially and then modified during the learning process.

3. A neural net is capable of independently converting the 'experiences' gained in the training into a complete set of weights ('weight matrix').

In most cases, only the weights are varied during the training process, that is, the topology of the neural nets remains unaltered. However, in special cases, the previously mentioned 'self-organizing maps' (SOM) are also used.

SOMs are models of neural networks which imitate the brain's capacity for self-organization, and organize their interconnect structure on their own, in accordance with simple rules. The "self-organizing map" is formed by an inner layer of neurons, which receives signals from neurons in an input layer. The inner layer is referred to as the map layer. Each neuron in the input layer is connected to each neuron in the map layer. For each input signal, the excitation is concentrated on one section of the neurons in the map layer. At the end of the learning phase, the position on the map of the most strongly excited neurons is related to significant features of the input signals, with similar input signals leading to adjacent excitation locations on the map. In other words, the map constitutes a spatial representation of characteristic features of the input signals.

The mathematical model of a self-organizing process of this kind was formulated by T. Kohonen. It is therefore also referred to as a "Kohonen feature map".

Further details on neural nets can be found in the pertinent literature. Particular reference is made to the book "Neuronale Netze, Grundlagen und Anwendung" ("Neuronal Nets, Principles and Application") by Klaus-Peter Kratzer, Carl Hanser Verlag (Publishers), Munich and Vienna (1990), and to U.S. Pat. No. 4,965,725, in which the function of a neural net in connection with the recognition of malignant cell structures in photomicrographs of cytological samples is illustrated and explained. This patent also contains a comprehensive list of relevant literature. Results of fundamental research on neural nets had already been published in the 1950's. Since the beginning of the 1980's, they have found increasingly widespread use in areas concerned with image processing and the related tasks of recognition and classification of data patterns.

A survey of the application of neural networks in chemistry is to be found in the article "Neural networks: a new method of solving chemical problems or just a passing phase?" by J. Zupan and J. Gasteiger, *Analytica Chimica Acta*, 248, 1–30 (1991). Insofar as this publication deals with analytical problems, these refer to the following applications:

Spectroscopic data (spectra in the UV, the visible, and the IR ranges) are evaluated; cf. P. J. Gemperline et al., "Nonlinear multivariate calibration using principal components regression and artificial neural networks", *Anal. Chem.*, 63, 2313–2323 (1991), and J. Zupan, "Can an instrument learn from experiments done by itself?", *Analytica Chimica Acta*, 235, 53–63 (1990).

The signals from an arrangement consisting of several electronic detectors (in particular ion-selective electrodes and gas sensors) are evaluated with the aid of a neural network; cf. K. C. Persaud, "Electronic gas and odour detectors that mimic chemoreception in animals", *Trends in Analytical Chemistry*, 11, 61–67 (1992), and M. Bos et al., "Processing of signals from an ion-selective electrode array by a neural network", *Analytical Chimica Acta*, 233, 31–39 (1990).

The strength of classical computer systems lies in the very accurate and rapid execution of a predetermined sequence of precisely defined commands (algorithm). The algorithm may concern both a calculation problem and an organizational problem or logical connection. In this respect, computers are far superior to the human brain.

However, the familiar conventional computers encounter difficulties in problems that cannot be solved by following precisely predetermined rules, but require associative abilities. They are therefore far inferior to the human brain for solving non-algorithmic problems, such as, for example, pattern recognition or classification problems. Neural net systems are suitable for such tasks. The crucial point of the applications of neural nets used hitherto (including those used in the field of chemistry, as mentioned above) therefore lies in the setting of tasks involving association, classification, or assessment. neural nets are, however, apparently disadvantageous in that they are restricted to areas of use with a high tolerance of errors and limited quality requirements with regard to the results.

The analysis of medical samples by means of autoanalyzers is, on the other hand, an area in which high quality demands are made on the results because of their importance for the health of the patients. Despite this apparent antithesis, it was found that, during use of the invention, outstanding results can be obtained even in this area with the use of neural nets.

In a training phase, which is also referred to here as the training stage, of the process according to the invention, at least one measured value R or at least one measurement result derived from several measured values $R_i$ is applied to the input of the neural net as the input variable for a sufficiently large number of samples for which the analytical result A is known. In the majority of applications the analytical result A or a known auxiliary value connected with the latter is applied to the output of the neural net.

A derived measurement result, in this sense, is a value derived from several measured values by a predetermined defined algorithm (which can be called the derivation method). Examples are the slope, the curvature, or the roughness of a kinetic R(t) calculated by certain (known) approximation formulae from values $R_i(t_i)$ measured at various times.

An auxiliary value, in this sense, may be a numerical value or a logical value linked with the analytical result, and, as a rule, serves to improve the quality of the analytical result A. One important example is an error code, which indicates whether the measured values or measurement results applied to the neural net input contain indicia of the presence of an error.

The input variables are adapted to the neural net input by normalizing them, where the highest measured value occurring is expediently taken as equal to 1.

In certain circumstances, it may be convenient to apply information on the state of the apparatus or of reagents to the neural net input as an additional input variable in the training stage. This includes, for example, the temperature of the surroundings, the age of the reagents, absorption properties of the reagents, etc. The use of a neural net therefore allows the determination of the analytical result A through the use of, in addition to the measured values and measurement results derived from these, information which may be considered with classical evaluation algorithms.

Neural nets are in practice at present predominantly implemented as software simulations for sequentially operating computers ('von Neumann architecture'). Such neural net simulations were successfully used in trials of the present invention. It is to be assumed that, with special hardware components supporting the resolution of neural nets problems by parallel processing, equivalent or even better results are obtainable.

The neural net training is generally carried out under supervision, i.e., the structure of the neuron layers and of the neuronal interconnects (topology) of the network is fixed beforehand. Likewise, predetermined propagation, activation, and output functions are used during the training. The course of the training can be influenced by a number of parameters such as learning rate, momentum, and noise factors. The method of artificial noising of the input takes account of the real situation, namely that determination of measured values is subject to experimental error. Noise components are superimposed here on the input values.

Various methods of assessing learning success are known. The cross-validation method, in particular, was used in the invention, i.e., a subset from a pool of sets of neural net input variables of known output is generally used for training, and the rest of the pool data are used for subsequent testing of the neural net for correct output, where the training subsets are sequentially 'permutated through'. The number of correct and incorrect outputs is then assessed. In a few simple cases, the end of the training can be defined by the value of a calculated error function, provided in the neural net software, dropping below a defined level or by the attainment of a specified quality or stability of the relation between input and output.

It can also be expedient in some cases to use the above-mentioned 'self-organizing maps' (SOM) instead of the described supervised learning. In contrast to a classical neural net, in the training stage, in which measured values or measurement results derived from them are in each instance applied at the input of the neural net, no analytical results or auxiliary values associated with them are applied at the output of the SOM. Instead, the SOM recognizes characteristic structures in the signals applied at its input and assigns them to positions in its map layer. In the context of the invention, it was found that, for particular applications on autoanalyzers, this "nonsupervised learning" with the aid of an SOM is advantageous. The following explanations, however, refer essentially (unless otherwise indicated) to "supervised learning" with the aid of a classical neural net.

After completion of the training stage, a certain network topology and a weight matrix are fixed. The result of the training may therefore be expressed quantitatively in the form of parameters of the network topology (preselected or found by self-organizing) and as a weight matrix. It is characteristic of the present invention that such a result is used in the analysis method claimed in the invention.

The training of a neural net required for the invention can be carried out both by the manufacturer of the reagent system used for the analysis and also on the autoanalyzer itself (with the aid of an neural net system integrated with or connected to the apparatus). In the first-named case, a particularly large database (e.g., from development and trials of the test and from quality control, which is usually carried out with the aid of a large number of samples of known concentration) is available as a training basis for the neural net. Training on the autoanalyzer has the advantage of the possibility of considering specific factors for the particular apparatus and its settings, and possibly, systematic measurement errors. A combination of two substages of the neural net training has proved particularly advantageous in which the first substage, which leads to a basic adaptation of the neural net, is carried out by the manufacturer of the reagent system, whilst the second substage is carried out as further training on the autoanalyzer for considering factors specific to the apparatus.

It becomes apparent that a training stage is not necessary in each individual analysis, but that it suffices if at least one neural net training is carried out in connection with the development of the test (that is, of the reagent system and its directions for use). However, it is often advantageous to carry out a neural net training at least for each manufactured batch of the reagent system and possibly to supplement this by additional further training stages on the autoanalyzer.

After completion of training, unknown outputs can be calculated from experimental input variables (measured values or measurement results) from the network topology, the utilized functions, and the interneuronal weight coefficients and neuron base potentials optimized in the learning phase. This result of the neural net training is used, in accordance with the invention, for the analysis. This can basically happen in such a way that exactly the same input variables (measured values and/or measurement results derived from these by the same methods as in the training stage) are applied at the input of the optimized neural net and, by using the weight matrix determined in the training, the analytical result A and/or the auxiliary values used in the neural net training are produced at the output of the neural net in the analysis of a sample for which the analytical result A is not known. This method is, however, relatively complicated.

As an alternative, many neural net simulation programs have special modules which, after completion of neural net training, make it possible to develop for utilization of the results, independent programs containing the network parameters and the optimized weight matrix as constants and that make an economic processing of the input values to the output values possible.

The invention particularly concerns cases of application in which several measuring signals $R_i$ of the same physically measurable quantity X are measured at various measuring times $t_i$ so that they describe a time-dependent alteration of the quantity X (kinetic). In this case, a number of measured values $R_i$ (determined one after the other) can be stored and simultaneously applied to the neural net input during training so that the total information on the kinetic can be processed in one learning cycle of the neural net. Instead of, or in addition to, this, derived measurement results can be applied to the neural net input calculated from values measured at various measuring times, according to a further preferred embodiment of the invention. Such measurement results derived from kinetics include, for example, curve slopes or curvatures, as well as positions of extreme values or turning-points of the time-dependent alteration of the measured value R(t). These two preferred measures can obviously be combined, so that measured values $R_i(t_i)$ and measurement results derived from these, such as curve slopes or curvatures, are applied simultaneously at the neural net input.

The invention has particular advantages in analyses based on the measurement of reaction kinetics. It was found that it is possible to describe, with sufficient reliability, systems which, because of their complexity, are not open to a classical mathematical analytical solution. In addition, the invention provides for the possibility of shortening reaction times in kinetic determinations through evaluation of partial regions of the kinetic reaction which is of great importance, particularly in immunochemical tests.

These and other objects, features and advantages of this invention will be apparent from the following detailed description of illustrated embodiments thereof, which is to be read in conjunction with the accompanying drawings.

DETAILED DESCRIPTION OF THE PREFERRED EMBODIMENTS

Figure 1:
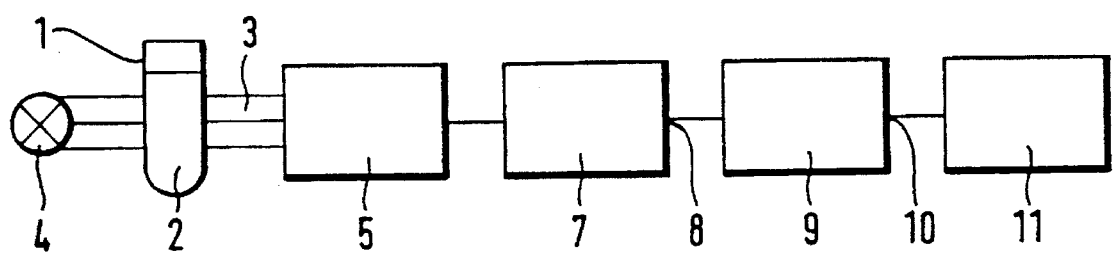
FIG. 1 is a block diagram of an autoanalyzer for carrying out the method of the invention.

FIG. 1 shows, in a generalized form, the formal structure of an autoanalyzer. The sample 2 in a cuvette 1 is permeated by a ray of measuring light 3 issuing from a light source 4. The measuring light ray 3 is a measure of the absorption by the sample 2, which in the example case forms the measurable quantity X. It falls on a detector 5, for example, a phototransistor, the output signal of which is applied to a measuring signal-processing circuit 7. This comprises, for example amplifiers, filters, and process signal converters which amplify and process the measuring signal in known manner, so that a measuring signal, the value of which forms the measured value R, appears at the output 8 of the measuring signal-processing circuit 7.

The measured value R is applied in analog or digital form to the input of a processing unit 9, which serves to determine, from the measuring signal, an analytical result A, which is led from its output 10 to an output unit 11, (for example, a display screen or a printer) where it can be displayed. The processing unit can basically consist of analog electronic or digital electronic hardware. In practice, it usually consists, according to the current state of the art, of a microcomputer system with suitable operating and application software. The processing stage (which in total comprises the processing of one or more measured values R to the analytical result A), carried out by means of the processing unit 9, often consists of several substages. These may comprise the derivation of measurement results by means of predetermined defined methods from several measured values $R_i$, which are then further processed.

The determination of the concentration C of an analyte in a sample from measured values R is described below as a first practical embodiment of the invention.

The functional relationship between an input variable Y (the measured value R or a measurement result derived from several measured values) and the concentration C is described by a calibration curve $Y=f(C)$. The calibration curve is determined by analyzing samples of known concentration ('standards'). The parameters of a function that describe the calibration curve are determined from the resulting Y,C pairs with the aid of a known mathematical method (usually a linear or non-linear regression).

When a neural net is used for the calibration in accordance with the invention, the values R are applied in the learning cycle to the input, and the known concentrations C, measured with the standards, are applied to the output of the neural net. When only one measured value is determined in each analysis in the analysis process, a neural net with only one neuron in the input layer is used. If several measured values, which, for example, describe the course of a kinetic with time, are determined on each sample, the neural net has a corresponding number of neurons in it input layer. Measurement results derived from kinetics can also be used as input variables for the training and the sample evaluation instead of the original measured values.

Figure 2:
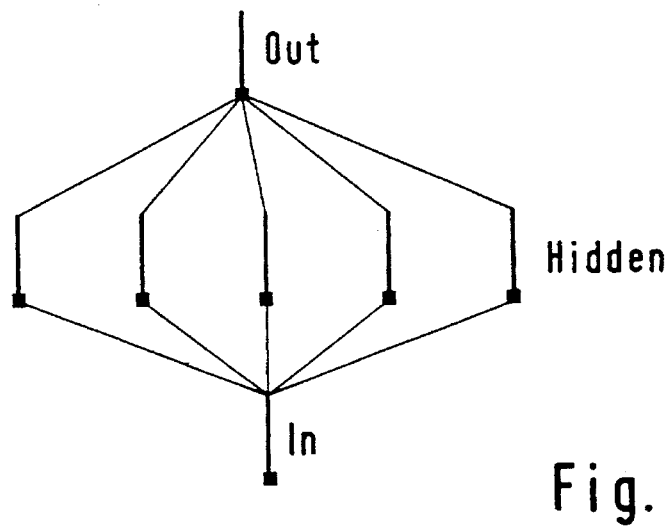
FIG. 2 is a graphical representation of the topology of a neural net used in a preferred embodiment of the invention.

The net topology of a neural net suitable for calibration is shown in FIG. 2. It consists of an input layer with one neuron, to which the normalized measured values for a standard are applied in the training, and an output layer likewise with only one neuron, to the output of which the normalized known concentration of the respective standard is applied. Between these, there is a unidimensional hidden layer, which, in the illustrated case, has 5 neurons.

The calibration and concentration determination with the aid of a neural net has especially the following advantages over the classical method of calibration:

Not all concentration/measured value relationships can be sufficiently well approximated by mathematical functions. In some cases, there is no analytical solution for the evaluation function, or this function is not defined over the entire concentration range. Classical calibration methods generally require a monotonous dependence of the calibration input variable Y on the concentration. If this monotony criterion is impaired, the function is no longer unambiguously defined, which results in failure of classical methods of calibration.

When a neural net is used, measurement results, such as measured value differences, curvatures of curves, and integrated values, that are derived from the measured values, can, as already mentioned, also be applied without any problems to the neural net input instead of the measured values. These may possibly show a better correlation to the concentration C than the actual measured value R. This can be simply tested in the neural net training by applying various measurement results derived from the measured values to the neural net input. Practical testing has shown that the reaction times in immunochemical tests can be shortened by these improvements.

According to a modified embodiment of the invention, the calibration can be carried out with a combination of a classical calibration function and a neural net. This is particularly advantageous when the calibration function is selected only on the particular analysis apparatus depending on its state and/or the state of the reagents.

The combination of a classical calibration function with a neural net training is advantageous, for example, in diagnostic tests, the calibration curve of which changes its position and shape depending on stresses such as storage temperature. The manufacturer of the test can carry out with these reagents series of defined stress tests that simulate the exposure to which the reagents are subjected in the laboratory and the alteration of the calibration curve associated with this. Complete calibrations are carried out at defined investigation times $t_i$ with suitable (classical) calibration methods. A neural net is then trained in such a way that the time intervals or stress values on which the stress tests are based are applied to the neural net input, and the function parameters of the calibration curves thus obtained represent the theoretical output. The stress values occurring in practice are input manually or automatically in the laboratory. The then valid set of function parameters is calculated by the neural net. In the same way, differences from apparatus to apparatus found by the manufacturer can be allowed for by suitable training without involving laboratory personnel.

The method of the invention is particularly suitable in cases that cannot be solved, or can be solved only with great difficulty, by classical calibration. Prime examples of this are cases in which the great majority of the analyte concentrations determined in patients' samples lie in a relatively narrow concentration range, though individual patient samples exhibit very much higher or lower values. With such parameters there is the difficulty of obtaining a sufficient quantity of standards for the calibration in the entire medically relevant concentration range, including the above-mentioned extreme values, because in many cases the standards must be obtained from the blood serum of volunteer donors, and these, of course, exhibit extreme concentration values only in exceptional cases. The present invention proves advantageous for such cases, as it has been found that it is sufficient for the neural net training to be carried out predominantly only with the standards in the frequently occurring concentration range and then to carry out further training with just a few standards in the extreme measured value range. When using classical calibration methods it is not permitted to extrapolate a calibration curve in this way into a region in which the connection between C and Y is not ensured by a sufficient number of standards. The concentration was reliably determined even in the 'extrapolation range' according to the invention with the aid of a neural net.

Figure 5:
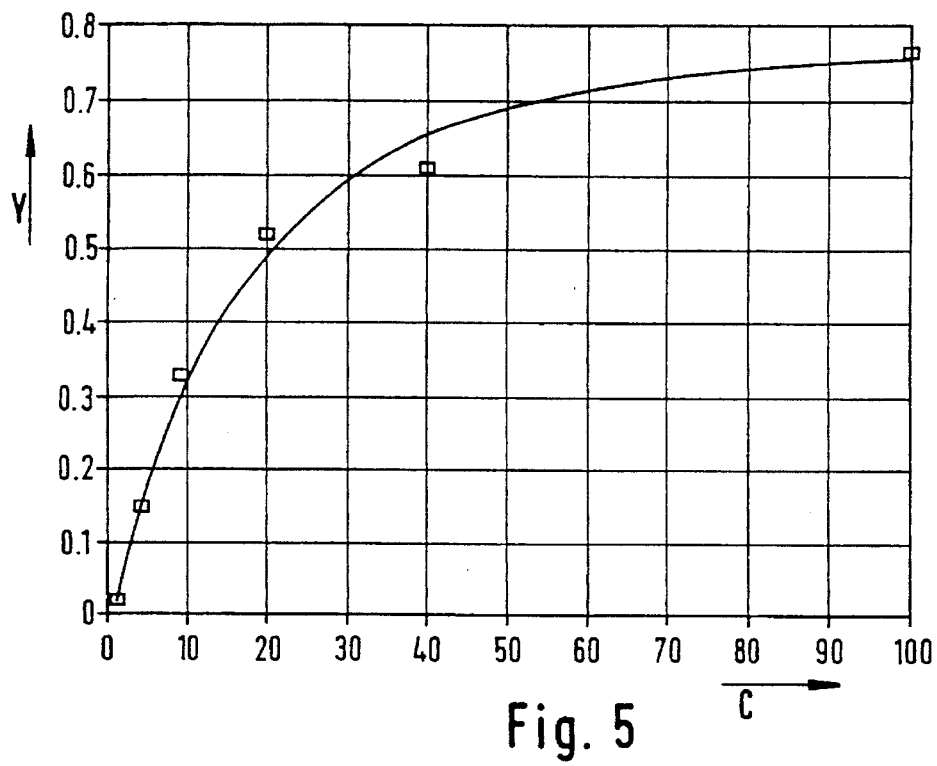
FIG. 5 is a graphical representation of a calibration curve.

A second problem case in which the invention is valuable relates to analyses using a non-linear calibration curve which has a flat asymptotic course in the region of high concentrations (FIG. 5). A reliable, albeit coarser, concentration assignment was obtained even in the asymptotic part of the calibration curve by using the method of the invention.

Figure 6:
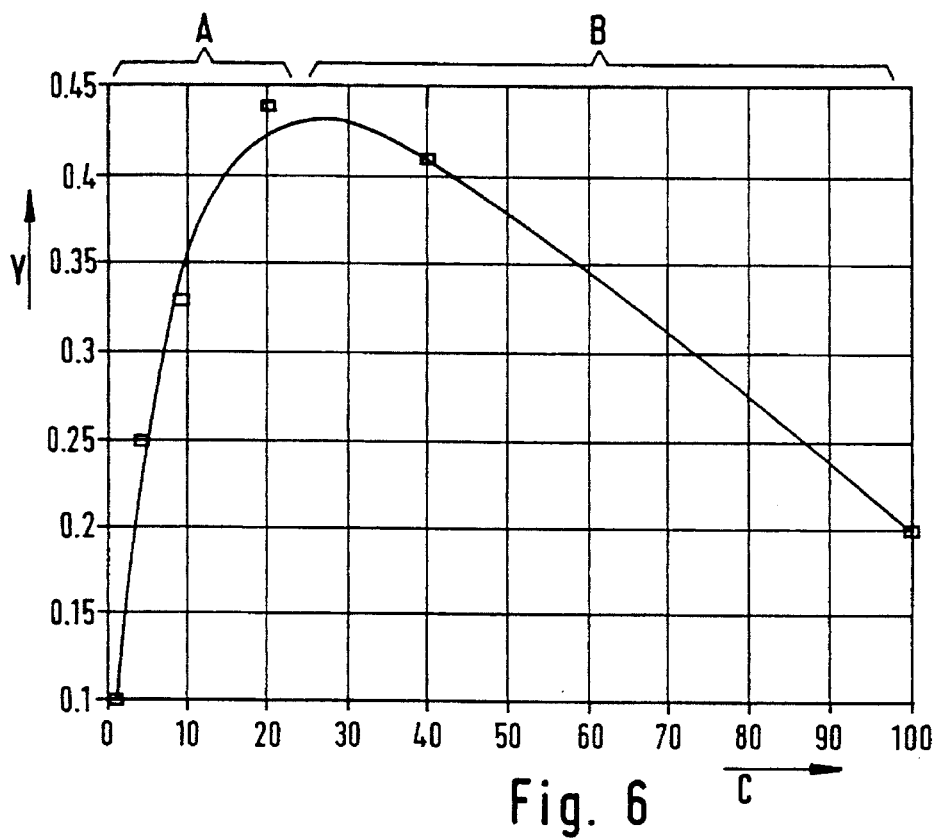
FIG. 6 is a graphical representation of a calibration curve.

A third example of problematic calibration curves is represented in FIG. 6. Here, the relation between the input variable Y and the concentration C is not monotonous. In this case, no definite assignment of a measured Y to a concentration C is produced when a classical calibration is used. A definite assignment is, on the other hand, possible with the aid of a neural net if, for each concentration, not just one measured value but several measured values $R_i$, which, for example, describe a kinetic $R_i(t_i)$, are applied to the neural net input. This will be discussed more fully below in connection with a further embodiment.

In semiquantitative analyses, the analytical result A, as was explained above, is not a concentration C, but a statement of an assignment of the sample to one of at least two different medico-analytical states, for example, 'positive' and 'negative'. The concentration boundary between medico-analytical states is usually fixed empirically and is known as the 'cut-off'.

One problem in the conventional determination of the cut-off is caused by the fact that this is in practice often dependent on the investigated patient group. In the invention, the conventional determination of a cut-off with the aid of a formula is replaced by an evaluation process based on a neural net in which measured values, or measurement results derived from these, can be applied to the neural net input in the same way as in the determination of a concentration C.

Figure 3:
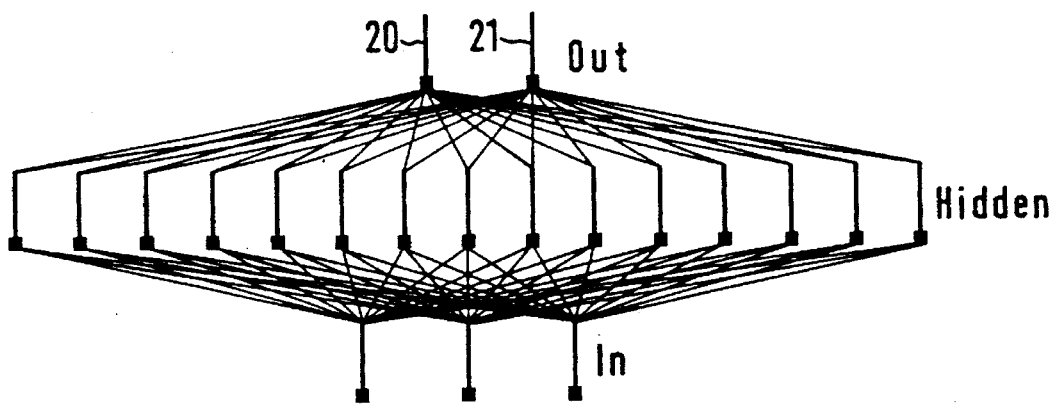
FIG. 3 is a graphical representation of the topology of a neural net used in a preferred embodiment of the invention.

In the training stage, the known correct assignment to the medico-analytical states is applied to the neural net output. While the concentration C has a continuous value spectrum, the medico-analytical states are an example of output variables of the neural net with a discrete value spectrum. In such cases, the output signal range of the neurons of the output layer is, as is customary in digital electronics, divided into two subranges, where the subrange above a limit value is interpreted as 'high' or 'logic 1' whilst the signal range below the limit value is interpreted as 'low' or 'logic 0'. The required number of neurons of the output layer results from this. One neuron, the output of which can assume two logic states, suffices in the output layer when the discrete value spectrum of the output variable can assume only two logic states. It may, however, also be expedient to work with a certain redundancy and to provide the output layer with more than the absolutely necessary number of neurons. FIG. 3 shows, by way of example, the topology of a neural net which is equipped to assign the results of a measurement to two medico-analytical states (e.g., positive and negative). In the training, the 'positive' state can, for example, correspond to the signal combination (1,0) at the outputs 20 and 21, whereas 'negative' corresponds to the signal combination (0,1). this procedure has the advantage that the inadmissible signal combinations (1,1) and (0,0) are recognized as erroneous.

In cases where the analytical result A or the auxiliary value has, as the output variable of the neural net, a value spectrum consisting of discrete values, a sigmoid activation function or a threshold value function is generally preferred, whereas in the case of a continuous value spectrum, a linear activation function as a rule proves best.

The training proceeds analogously to the previously described case (determination of a concentration), where, as the analytical result A, the correct assignment to the medico-analytical state, for example, positive or negative, is applied to the output. There is with this method the possibility of training the neural net with samples from a patient group corresponding in its composition to that of the patient group of the respective laboratory. The cut-off of semi-quantitative tests is thereby optimally determined in each instance without laborious investigations, and the number of falsely positive or falsely negative results is minimized.

It can also be expedient in this practical example to carry out the neural net training in two substages, where the basic training by the manufacturer of the test with a widely diverse range of patient samples is supplemented by further training on the (autoanalyzer) apparatus, where reference samples specific to the particular laboratory, which have a known assignment to a medico-analytical state, are applied to the neural net. Such reference sample measurements are customary in qualitative analyses.

A further practical example of the invention concerns cases in which the calibration curve Y=f(C) is not monotonous and hence the same value of an input variable Y (measured value or measurement result derived from this) corresponds to at least two subsections of the calibration curve with different values of the concentration C. In such cases, a definite assignment of a measured input variable Y to a concentration value C is not possible, or possible only with additional measures, using classical evaluation methods. Additional analytical determinations are generally necessary after dilution of the sample. Particularly important examples of such methods are homogeneous immunochemical analyses based on antibody precipitation, where the standard calibration curve is known as a 'Heidelberger curve'. The basic course of such a calibration curve is represented in FIG. 6. As these problems are known (see, for example, European Patent Application 0 148 463 and German Patent Application 4,221,807, the disclosures of which are incorporated herein by reference) they need not be explained more fully here.

In this case measured values, or measurement results derived from these, that comprise information on the kinetic R(t) of the measured value, are applied to the neural net input, the measured value being, in particular, the nephelometrically or turbidimetrically determined turbidity of the sample. As in the previous cases, the input variables of the neural net can be either a large number of measured values $R_i(t_i)$ determined at various times, measurement results derived from these, or a combination of these two types of input variable.

The correct assignment to a section of the calibration curve (subsections A and B being plotted in FIG. 6) is applied to the output of the neural net in the training stage as an auxiliary value linked to the analytical result. As the value spectrum of the output variable again is discrete here, the above explanations apply with regard to the neurons of the output layer.

Figure 4:
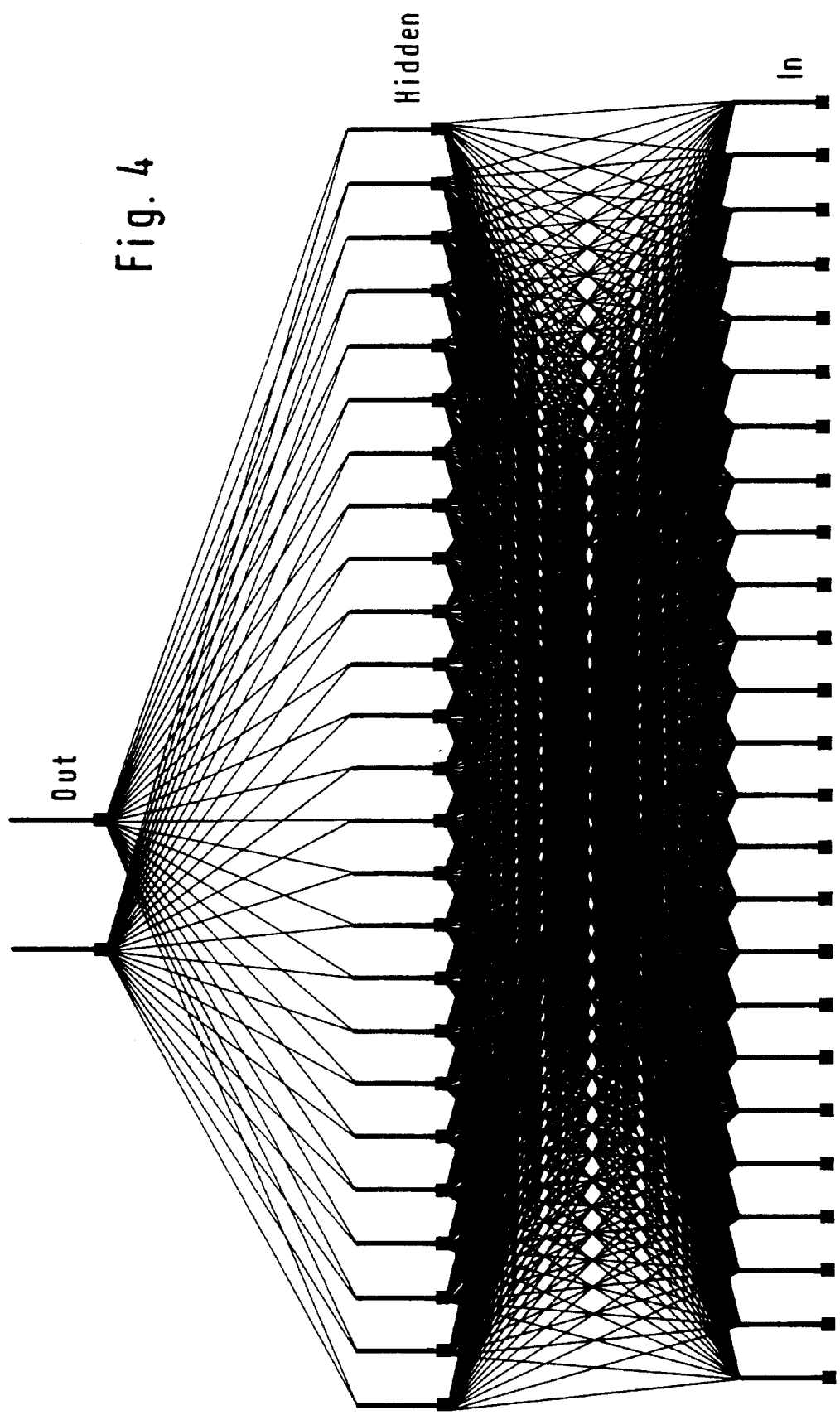
FIG. 4 is a graphical representation of the topology of a neural net used in a preferred embodiment of the invention.

FIG. 4 shows, by way of example, the topology of a suitable neural net for this practical application, in which the input layer has 25 neurons to which normalized extinction values (as measured values) or measurement results derived from them, which describe a measured reaction kinetic, can be applied simultaneously. The output layer has two neurons. A hidden layer of 25 neurons is sandwiched between them. The neuronal interconnects are provided between all the neurons of adjacent layers.

Trials have shown that, in this way, the assignment to subsections of the calibration curve is possible with sufficient reliability for practical purposes in the above-mentioned homogeneous immunochemical tests. This avoids the effort and expense of additional determinations, and increases the reliability of the analysis. This embodiment of the invention is of especial advantage in cases where the clinically relevant concentration range includes particularly high concentration values and hence, known methods, which avoid the ambiguity of the calibration curve, in particular, the use of a very high antibody concentration, are disadvantageous for economic reasons.

A further application of the invention is the detection of errors on automatic analysis systems. For reasons of quality assurance of diagnostic determinations as well as of legal provisions, there is great interest in providing error detection routines in automatic analysis systems. With a high degree of automation of the apparatus, these routines must be more complete and reliable.

The possibilities for detection of errors with the aid of conventional methods are, on the other hand, limited by the extraordinary complexity of the problems. The multiplicity of diagnostically important analytes that have to be determined with the same automatic analysis system, the differences in concentration, and the complex procedures in the analysis (sample treatment, addition of reagent, reception and assignment of measuring signal) make it difficult, and sometimes impossible, to detect the possible error constellations in a manner that can be correctly processed by conventional electronic apparatus.

It was found that, with the invention, neural nets can be used to advantage for the recognition of errors on autoanalyzers. Here the training stage for learning of the error pattern by the neural net must be completed before commencement of the measurements in the clinical laboratory. It is therefore preferably carried out by the manufacturer of the reagent system, particularly in order to make sources of error associated with the reagent system recognizable, where it may be of advantage to carry out further training on the autoanalyzer with regard to sources of error specific to the apparatus. For recognition of errors, the same input variables as in the above-mentioned application example of a non-monotonous calibration curve can be applied to the neural net input. Information on the kinetic is thus also available to the neural net in this case.

In this instance, the training can proceed in such a way that an error code that distinguishes disturbed kinetics from sets of undisturbed kinetics is applied to the output of the neural net. Samples or reagents in which typical error states have been deliberately induced can, for example, be used. One example consists of samples rendered low in oxygen in cases where the analysis requires an adequate oxygen content of the sample. Here the neural net is trained by always applying the error code 'Error' to the output of the neural net when a sample low in oxygen is being analytically determined, whereas with normal samples the state on the neural net output is 'No error'. A neural net with the same basic topology as in the previous example (FIG. 4) can be used here.

Trials have shown that, in this way, a reliable differentiation of erroneous kinetics from error-free kinetics is possible, although these often show nothing remarkable that could be immediately recognized as erroneous with conventional methods of measurement signal processing. Sources of error may be avoided, which could arise with conventional procedures, for example, by the reciprocal compensation of errors.

Error recognition is a particularly important example for the use of SOMs on autoanalyzers. Measured values, or measurement results derived from them, which describe the reaction kinetics, are thus applied to the input of a Kohonen feature map in a training stage for a large number of kinetics of different samples. This leads, as already described, to characteristic properties of the applied kinetics being displayed spatially in the map layer of the SOM. In the context of the invention, it has been established that, in this way, a reliable separation of erroneous kinetics from error-free kinetics is achieved in their display in the map layer of the SOM. This makes it possible to define specific sub-areas on the map layer as erroneous or error-free and, by application of the SOM in the on-going analysis, to recognize and eliminate erroneous kinetics.

A further interesting area of use of the invention is the prolongation of the duration of use of reagents. The reagents of clinical analysis systems undergo an aging process. Inaccuracies are, in practice, reduced to an acceptable level by stipulating relatively short shelf lives. However, this results in considerable expenditure.

In the context of the invention this expenditure can be considerably reduced if one or more auxiliary values describing the aging of the reagents (in the simplest case, their shelf life) are applied to additional neurons in the input layer during the neural net training and the training is carried out with reagents of varying ages. It is thus possible to proceed in such a way that, on each occasion, the actual measured values or measurement results are applied to the input, and the theoretical measured values for fresh reagent are applied to the output, using the neural net to correct the measured values. Preferably, however, calibration and correction for reagent aging are combined, the previously described calibration procedure being expanded simply by providing additional input neurons for one or more auxiliary values which describe the aging of the reagent and by extending the training to reagents of different ages.

Finally, the simultaneous analysis of several analytes in a sample is a further area of use of the invention. Whilst it is already a widespread practice in general chemical analysis to determine several different analytes simultaneously in one sample with suitable methods (electrophoresis, for example,) this has not so far been customary in the analysis of medical samples. In conventional evaluation methods, the courses of the calibration curves are too non-specific to allow evaluation for two components separately from the superimposed calibration curves of two tests.

The invention can also be used to advantage in this case by applying, to the input of the neural net, measured values or measurement results derived from these as input variables, as in the preceding cases. Input variables that describe the kinetic are again preferably used. The two concentrations with a continuous value spectrum can, in this case, be applied as output variables directly to two neurons of the output layer in the training stage.

The following Examples serve for the further illustration of the invention.

EXAMPLE 1

The LH (human luteinizing hormone) parameter was determined in patient samples with the aid of a neural net by measuring 15 LH standards (samples with known LH concentration) in three series with the Enzymun® ES 300 Test System of Boehringer Manneheim GmbH, Mannheim, Germany. This is an analysis in which one extinction value 18 measured for each concentration. The measured value pairs of concentration C and the respective extinction value E were normalized ($C_0=0$, $C_{max}=1$, $E_0=0$, $E_{max}=1$) and used for training the neural net.

The Neural Works Professional II program of Neural Ware Inc., Pittsburgh, Penn., USA, installed on a standard personal computer with an Intel 80486 processor, was used here.

The network structure and the learning parameters were optimized as follows:

The net topology corresponded to FIG. 2. The learning rate of the neural net was set at 0.9, and the momentum at 0.6. A linear output function was chosen for all neurons. A back-propagation algorithm was used in the training. A total of 30,000 learning cycles was run, until the error function showed a maximum error of less than $10^{-4}$. No use was made of the program's capability of adding a noise signal.

After completion of training, an independent C-program, containing as constants the parameters of the network topology and the weight matrix, was generated with the aid of the Neural Works Professional II program. the size of this C-module amounted to about 2 KBytes.

Figure 7:
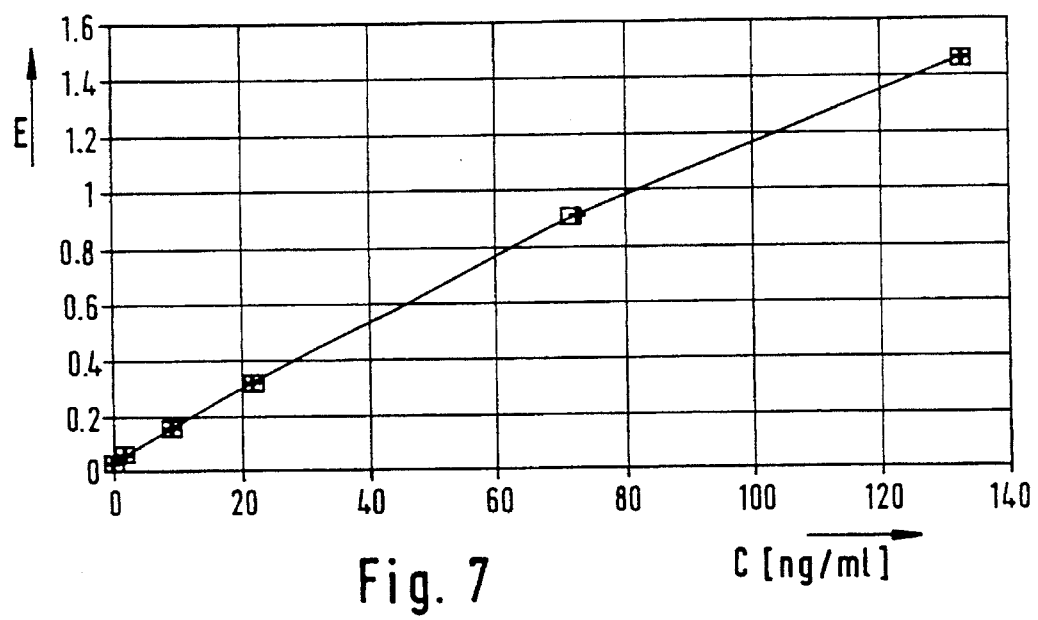
FIG. 7 is a graphical representation of a calibration curve.

The LH concentration in samples with an unknown analyte content was measured with the Enzymun® LH ES 300 Test System. The result of the neural net training was used here, in such a way that the measured extinction values were normalized with the normalization factor used in the training, and the sample concentrations were calculated from this with the aid of the C-program. Within the limits of the error tolerance of the test system, the concentrations thus determined were up to 100% correct. The relation between the concentration C and the extinction E (as calibration input variable Y) is represented in FIG. 7, in which the rectangles indicate the extinctions measured with standard samples of known concentration. The plotted line corresponds to a calibration curve determined on the basis of a classical phenomenological model. The crosses indicate concentration values determined in the described manner with the aid of a neural net. Complete agreement can be recognized.

EXAMPLE 2

A neural net was used as follows to determine concentrations in the case of a non-monotonous calibration curve. Samples with known concentrations of the analyte Ferritin (standard supplied with the reagent system as well as patients' sera with known Ferritin content) were used here with the aid of the Tina-quant® Ferritin Test System and the Hitachi-717® autoanalyzer (both supplied by Boehringer Mannheim GmbH). Two different manufactured batches of the reagent system were used and compared.

The test is a homogeneous immunochemical test, the calibration curve of which has the form of a "Heidelberger curve". The inversion of the calibration curve above a certain concentration value is also known as the 'hook effect'.

Figure 8:
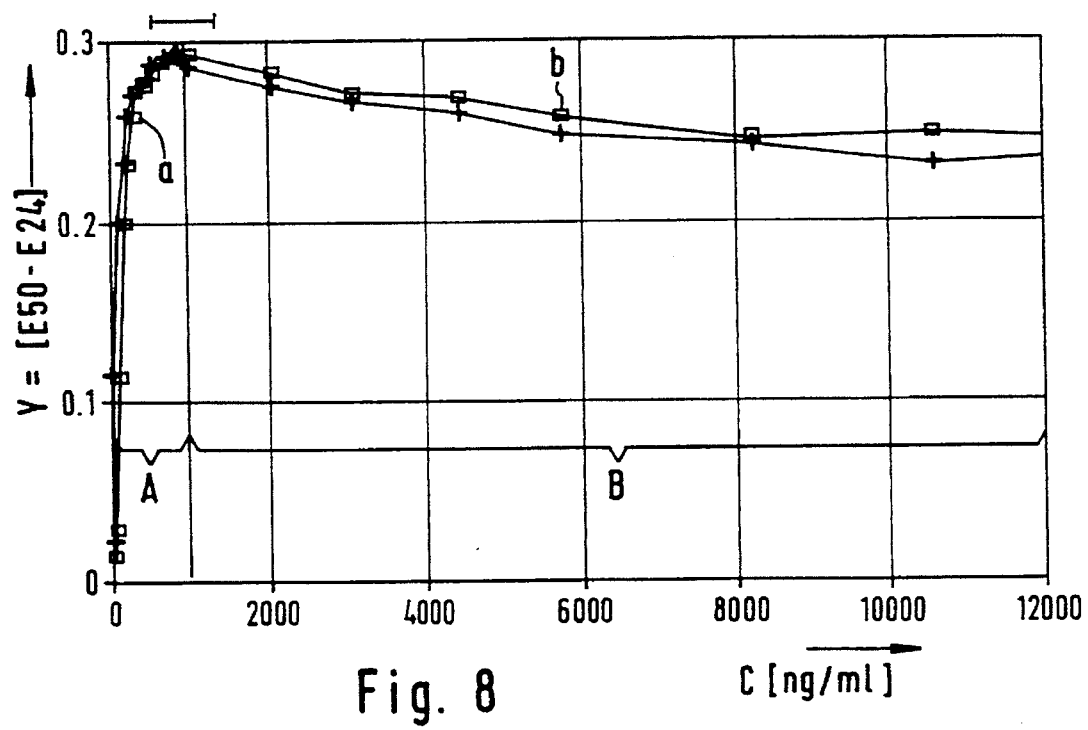
FIG. 8 is a graphical representation of a calibration curve.
Figure 9:
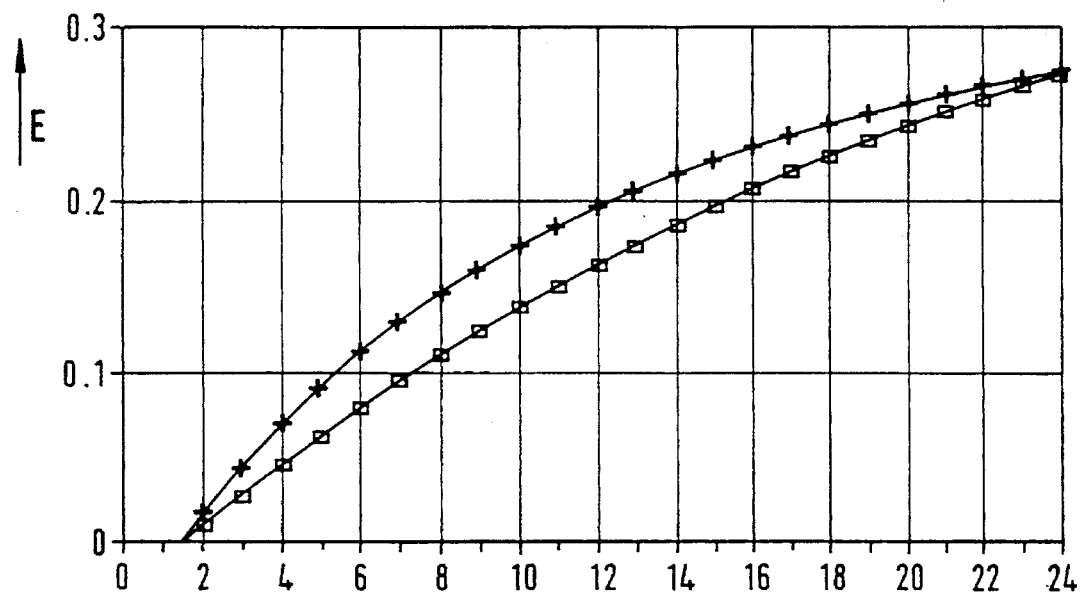
FIG. 9 is a graphical representation of kinetics for the calibration curve shown in FIG. 8.

Here the extinction kinetics were monitored by regular measurements at 12-second intervals. The difference between the 50th and the 24th extinction measurements was used as the calibration input variable Y. FIG. 8 shows the relationship between the input variable $Y=E_{50}-E_{24}$ and the Ferritin concentration C in the form of a non-monotonous Heidelberger curve with the subsections A and B. Two different reagent batches are marked with rectangles and crosses. FIG. 9 shows kinetics of the measured points designated by a and b in FIG. 8. It can be seen that despite practically identical curves of the calibration input variable Y, different kinetic courses are shown for these measured points (with the concentrations 350 ng/ml for a and 6000 ng/ml for b).

BrainMaker Professional® software of California Scientific Software, implemented on a standard PC with Intel 80383/80387 processors, was used as the neural net simulation.

The following net structure and learning parameters were set: The net topology (FIG. 4) consisted of 25 neurons in an input layer, to which the normalized extinctions ($E_{tmin}=0$, $E_{tmax}=1$) were applied. The output layer had 2 neurons, to each of which one (0,1) value for the assignment to the subsections A or B of the calibration curve was applied.

Between the input and output layers there was a unidimensional hidden layer with 25 neurons. The learning rate was 1.0, and the momentum was set at 0.9. A sigmoid activation function was chosen for all neurons. A counterpropagation algorithm was used in the training. A total of 150 learning cycles was run, until the error function showed a maximum error of less than 0.1. A noise function, with randomized disturbances of 0–20% relative to the extinction values, was incorporated.

After completion of the training phase, an independent C-program, containing the parameters of the network topology and the weight matrix as constants, was generated with the aid of the BrainMaker Professional® program. The size of the C-module, including the data matrix, in the example case was 21 KBytes.

The function was tested by measuring both undiluted and diluted samples containing various Ferritin concentrations with the named reagent system and autoanalyzer. The output values of the neural net, namely the assignment to the subsections A and B of the Heidelberger curve, were determined from the standardized extinction values with the aid of the C-program. The results were compared with the results of experiments in which the samples were correctly assigned to the subsections and correct concentration values were therefore obtained.

EXAMPLE 2a

Using the set of data from Example 2, the reduction of measurement time for kinetic analyses made possible by the invention was investigated. In each instance, only the first 24, 23, 22, 18 and 14 measured values were used from the kinetic consisting of a total of 25 measurement points. The same program as in Example 1 was used as the neural net simulation.

In this case, the neural net had a number of neurons in the input layer corresponding to the number of measured values, and one neuron in the output layer. Between the input layer and the output layer there was a one-dimensional hidden layer with 9 neurons. The learning rate was 0.3, and the momentum was set at 0.01. A hyperbolic tangent was used as the activation function for all neurons. During the training, a back-propagation algorithm was used.

Here, too, an independent program was generated with the aid of the neural net simulation program, in which the network topology parameters resulting from the training and the weight matrix were included as constants.

It was established that, even with only 14 measurement points, the analyte concentration was well reproduced. With the exception of the smallest concentration values (which are at the limit of the resolution capability of the system), the deviation amounted to less than 5%.

EXAMPLE 3

To test the use of a neural net for recognition of errors, analyses were carried out with the aid of the triglyceride-GPO-PAP test (Boehringer Mannheim GmbH). 350 extinction/time curves of high and low triglyceride concentrations were investigated here. Normal and artificially oxygen-depleted reagents were used. The Hitachi-717® was again used as the autoanalyzer.

ANSim® Neural Net Software of Science Applications International Corporation, which was again implemented on an 80386/80387 PC, was used as the neural net simulation in the example.

The following net structure (similar to FIG. 4) and learning parameters were set up: The input layer consisted of 50 neurons, to which the normalized extinction values $E_{tmin}=-0.5$ and $E_{tmax}=0.5$ were applied. The output layer consisted of two neurons, to which was applied one (0,1) value each for the 'normal' kinetic and for the 'disturbed' kinetic. A unidimensional hidden layer of 25 neurons was sandwiched between them. The learning rate was 0.01, and the momentum was set at 0.6. A sigmoid activation function was chosen for all neurons. A back-propagation algorithm was used in training. A total of 350 learning cycles was run, until the error function showed a mean error of less than $2 \times 10^{-3}$. No noise function was included.

Testing for correct error detection was carried out with a further 30 samples, which, in other investigations, had sometimes shown conspicuous kinetics. 50 extinction values from one kinetic were stored here in a database and made available to the ANSim software. The evaluation was carried out with the same neural net program, using the structure and weight matrix ascertained with the training run. The results were compared with graphic representations of the extinction/time relationships, from which any disturbances are immediately apparent. In all investigated samples, the result of the automatic error detection by the neural net and that of the graphic evaluation agreed.

EXAMPLE 3a

Using the same test as in Example 3, the use of an SOM (Kohonen feature map) for error detection was investigated. In this case, an experimental set of 355 reaction kinetics was first divided up by an experienced technician into normal and disturbed kinetics. This classification yielded 277 normal and 78 abnormal kinetics. The anomalies were to be found in a wide variety of technical and chemical disturbances of the reaction process, which occurred with varying frequency and were reflected in the kinetics.

The simulation of the SOM was provided with the aid of the same program packet as in Example 1. The input layer had 50 neurons, to which the normalized extinction values described in Example 3 were applied. The map layer had 40 neurons. On completion of the training with the 355 kinetics referred to, a clear division of the excitation intensity into two sub-areas of the map layer resulted. The test revealed that with few exceptions one sub-area (the larger) contained the normal kinetics (274 out of 277), while the second area contained the abnormal kinetics (74 out of 78).

EXAMPLE 4

The hepatitis parameter HBE was measured in a number of laboratories, each dealing with 150 to 250 patient samples, to test the application of a neural net to the assignment of measurement results to the medico-analytical states of a qualitative test. Measured values (extinction kinetics) were also measured on two reference samples ('controls') to which the states positive and negative were assigned. The measured extinction values were normalized separately for the laboratories as described in Example 1. The neural net system as in Example 2 was used.

The net structure consisted of three input neurons (for the extinction of the sample, the positive control, and the negative control), a hidden layer of 15 neurons and two output neurons (for positive and negative findings). The learning rate was 1.0, and the momentum was set at 0.9. No noise function was used. A sigmoid activation function was used for all neurons.

Figure 10:
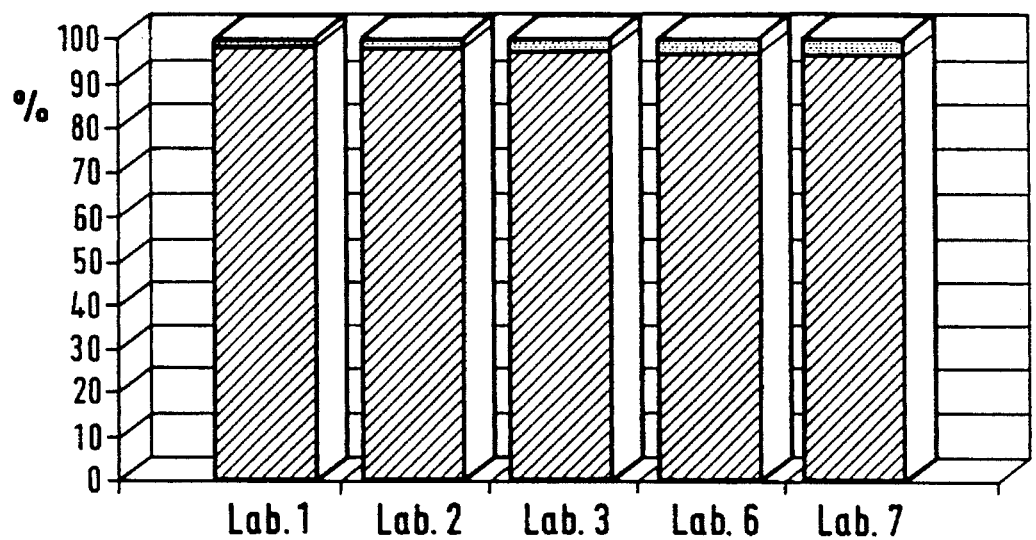
FIG. 10 is a graphical representation of the results of an assignment of measurement results to medico-analytical states.

After completion of training, the quality of the assignment was tested by classification of the samples within the Brain-Maker Professional® neural net simulator. The measured values from Laboratory 7 were used here for the training, the results of which were used for evaluating the measurement data of all the laboratories. The result is represented in FIG. 10. The number of correct assignments in the test data from all laboratories was greater than 95% and, in some cases, the proportion of incorrect assignments (falsely positive or falsely negative) was smaller than 1%, even better values being attainable by further optimization.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for the kinetic analysis of a component of a medical sample by means of an autoanalyzer to determine the concentration C of the component or a concentration-related parameter for the medical sample, comprising the steps of:

a. reacting the sample with a reagent system, the step of reacting the sample with the reagent system resulting in a time-dependent alteration in a physically measurable quantity X;

b. measuring the physically measurable quantity X at various measurement times $(t_i = t_1, t_2, \ldots, t_n)$ and determining therefrom a plurality of time-dependent input values for a specified sample, said plurality of time-dependent input values being selected from the group consisting of:

(1) several measured values $R_i(t_i)$ of the same physically measurable quantity X for a specified sample, (2) several measurement results derived from several measured values $R_i(t_i)$ for a specified sample, and (3) combinations thereof, and c. processing said plurality of time-dependent input values as defined in step b for the specified sample by means of a processing unit having a trained neural net and determining therefrom an analytical result A, wherein, for a specified sample, the analytical result A is the concentration C of a component or a concentration-related parameter for the sample; wherein the processing step further includes the step of using the trained neural net resulting from a neural net training, the neural net training including, for each of a large number of standard samples for which the analytical result A is known, applying to an input layer of a neural net a plurality of time-dependent input values as defined in step b;

wherein the neural net comprises a substantially parallel data processing system including a plurality of neuronal processing elements arranged in a distributed topology which includes at least:

(i) a plurality of layers, each layer having at least one neuronal processing element, the at least one neuronal processing element having an input and an output, one of the plurality of layers being an input layer comprising at least one neuronal processing element, said input layer having applied thereto a plurality of input signals corresponding to said plurality of time-dependent input values as defined in step b, another one of the plurality of layers being an output layer, comprising at least one neuronal processing element, said output layer providing an output signal corresponding to the analytical result A; and (ii) a plurality of neuronal interconnects, each neuronal interconnect connecting an output of a neuronal processing element in one layer to an input of a neuronal processing element in another layer, and having a weight which is modifiable during said neural net training.

2. A method according to claim 1, wherein said measuring step b further comprises measuring the physically measurable quantity X at various measurement times ($t_i=t_1, t_2, \ldots, t_n$) and determining therefrom several measured values $R_i(t_i)$ of the same physically measurable quantity X, the measured values $R_i(t_i)$ describing a time-dependent alteration of the measured quantity X, and applying to the input of the trained neural net at least one of the measured values $R_i(t_i)$.

3. A method according to claim 1, wherein said measuring step b further comprises measuring the physically measurable quantity X at various measurement times ($t_i=t_1, t_2, \ldots, t_n$) and determining therefrom several measured values $R_i(t_i)$ of the same physically measurable quantity X, determining at least one measurement result derived from at least two of the several measured values $R_i(t_i)$, and applying to the input of the trained neural net said at least one derived measurement result.

4. A method according to claim 1, wherein said neural net is a self-organizing neural net.

5. A method according to claim 1, wherein said neural net training further includes applying the known analytical result A to the output of the neural net whenever said plurality of time-dependent input values is applied to the input of the neural net for the standard sample.

6. A method according to claim 1, wherein said analytical result A is the concentration C of a component of the sample.

7. A method according to claim 6, which further comprises calibrating the processing unit for determining the concentration C from said plurality of time-dependent input values for the specified sample using the result of the neural net training.

8. A method according to claim 6, wherein said processing step further comprises determining the concentration C of the component of the specified sample in a measurement range which is greater than a concentration range covered by the standard samples by using the result of the neural net training.

9. A method according to claim 1, wherein said analytical result A is the concentration C of the component of the sample, and wherein the concentration C correlates with a calibration input variable Y derived from the time-dependent alteration of the plurality of time-dependent input values, where a calibration curve Y=f(C) is non-monotonous, so that the same value of the input variable Y corresponds to different values of the concentration C in at least two subsections of the calibration curve, and said processing step further comprises assigning at least one input variable Y determined from the plurality of time-dependent input values to one of the at least two subsections of the calibration curve by using the result of the neural net training.

10. A method according to claim 1, wherein said analytical result A is the assignment of the specified sample to one of at least two different medico-analytical states, and wherein said processing step further includes the step of assigning each of said plurality of time-dependent input values correctly to one of the at least two different medico-analytical states by using the result of the neural net training.

11. A method according to claim 1, wherein said processing step further comprises classifying each of said plurality of time-dependent input values into one of an erroneous measurement result category and an error-free measurement result category by using the result of the neural net training.

12. A method according to claim 1, wherein at least part of the neural net training is carried out by a manufacturer of the reagent system independently of the autoanalyzer.

13. A method according to claim 12, wherein the neural net training further includes a first substage and a second substage subsequent to the first substage, the first substage being carried out by the manufacturer of the reagent system and the second substage being carried out as further training on the autoanalyzer.

14. A method according to claim 5, wherein the neural net training further includes applying a known auxiliary value corresponding to the analytical result A to the output of the neural net whenever the plurality of time-dependent input values is applied to the input of the neural net for the standard sample.

15. A method for the kinetic analysis of a component of a medical sample by means of an auto analyzer and a neural net to determine the concentration C of the component or a concentration-related parameter for the medical sample, comprising the steps of:

(a) training the neural net, the step of training the neural net including the steps of:

(1) reacting a standard sample for which an analytical result A is known with a reagent system, wherein, for a specified sample, the analytical result A is the concentration C of a component of the sample or a concentration-related parameter for the sample, the step of reacting the standard sample with the reagent system resulting in a time-dependent alteration in a physically measurable quantity X for the standard sample;

(2) measuring the physically measurable quantity X for the standard sample at various measurement times ($t_i=t_1, t_2, \ldots, t_n$) and determining therefrom a plurality of time-dependent input values for the standard sample, said plurality of time-dependent input values being selected from the group consisting of:

(i) several measured values $R_i(t_i)$ of the same physically measurable quantity X for the standard sample, (ii) several measurement results derived from several measured values $R_i(t_i)$ for the standard sample, and (iii) combinations thereof;

(3) applying to the input layer of the neural net the plurality of time-dependent input values as defined in step a(2) for the standard sample, the neural net comprising a substantially parallel data processing system including a plurality of neuronal processing elements arranged in a distributed topology which includes at least: a plurality of layers, each layer having at least one neuronal processing element, the at least one neuronal processing element having an input and an output, one of the plurality of layers being an input layer comprising at least one neuronal processing element, the input layer being adapted for having applied thereto a plurality of input signals corresponding to said plurality of time-dependent input values as defined in step a(2) for the standard sample, another one of the plurality of layers being an output layer, comprising at least one neuronal processing element, said output layer providing an output signal corresponding to the analytical result A, and a plurality of neuronal interconnects, each neuronal interconnect connecting an output of a neuronal processing element in one layer to an input of a neuronal processing element in another layer, and having a weight which is modifiable during said neural net training; and (4) repeating steps (1) through (3) for a plurality of different standard samples for which the analytical result A is known, and thereby obtaining a trained neural net; and (b) analyzing a medical sample for which an analytical result A is unknown by using the trained neural net, the step of analyzing the medical sample including the steps of:

(1) reacting the medical sample for which an analytical result A is unknown with the reagent system, the step of reacting the medical sample with the reagent system resulting in a time-dependent alteration in a physically measurable quantity X for the medical sample;

(2) measuring the physically measurable quantity X for the medical sample at various measurement times ($t_i=t_1, t_2, \ldots, t_n$) and determining therefrom a plurality of time-dependent input values for the medical sample, said plurality of time-dependent input values selected from the group consisting of:

(i) several measured values $R_i(t_i)$ of the same physically measurable quantity X for the medical sample, (ii) several measurement results derived from several measured values $R_i(t_i)$ for the medical sample, and (iii) combinations thereof; and (3) processing the plurality of time-dependent input values as defined in step b(2) for the medical sample and determining therefrom the analytical result A for the medical sample, the step of processing including applying to the input layer of the trained neural net the plurality of time-dependent input values as defined in step b(2) for the medical sample.

16. A method of training a neural net for use in the kinetic analysis of a component of a medical sample by means of an autoanalyzer to determine the concentration of the component or a concentration-related parameter for the medical sample, comprising the steps of:

(1) reacting a standard sample for which an analytical result A is known with a reagent system, wherein, for a specified sample, the analytical result A is the concentration C of a component of the sample or a concentration-related parameter for the sample, the step of reacting the standard sample with the reagent system resulting in a time-dependent alteration in a physically measurable quantity X for the standard sample;

(2) measuring the physically measurable quantity X for the standard sample at various measurement times ($t_i=t_1, t_2, \ldots t_n$) and determining therefrom a plurality of time-dependent input values for the standard sample, said plurality of time-dependent input values selected from the group consisting of:

(a) several measured values $R_i(t_i)$ of the same physically measurable quantity X for the standard sample, (b) several measurement results derived from several measured values $R_i(t_i)$ for the standard sample, and (c) combinations thereof;

(3) applying to an input layer of the neural net the plurality of time-dependent input values as defined in step a (2) for the standard sample; and (4) repeating steps (1) through (3) for a plurality of different standard samples for which the analytical result A is known, and thereby obtaining a trained neural net; wherein the neural net comprises a substantially parallel data processing system including a plurality of neuronal processing elements arranged in a distributed topology which includes at least:

(i) a plurality of layers, each layer having at least one neuronal processing element, the at least one neuronal processing element having an input and an output, one of the plurality of layers being an input layer comprising at least one neuronal processing element, said input layer being adapted for having applied thereto input signals corresponding to said plurality of time-dependent input values as defined in step (2) for the standard sample, another one of the plurality of layers being an output layer comprising at least one neuronal processing element, said output layer being adapted for providing an output signal corresponding to the analytical result A; and (ii) a plurality of neuronal interconnects, each neuronal interconnect connecting an output of a neuronal processing element in one layer to an input of a neuronal processing element in another layer, and having a weight which is modifiable during said neural net training.

\* \* \* \* \*